United States Patent [19]
Giudicelli et al.

[11] 3,965,190
[45] June 22, 1976

[54] PHENYL PROPANONES

[75] Inventors: Don Pierre René Lucien Giudicelli, Fontenay-sous-Bois; Henry Najer, Paris, both of France

[73] Assignee: Synthelabo, Paris, France

[22] Filed: May 30, 1973

[21] Appl. No.: 365,181

[30] Foreign Application Priority Data
May 31, 1972 France ........................... 72.19515

[52] U.S. Cl. ............................. 260/592; 260/599; 260/609 R; 260/611 A; 260/570; 260/8 R; 260/293.9; 260/247.1 R; 260/247.7 A; 260/243 B; 260/247.7 Z; 424/298; 424/330; 424/248; 424/267; 424/246; 424/331
[51] Int. Cl.² .......................................... C07C 49/80
[58] Field of Search ..................... 260/592; 424/331

[56] References Cited
UNITED STATES PATENTS
3,748,361  7/1973  Rosenfeld et al. ................. 260/592
3,763,142  10/1973  Manning ............................ 260/592

FOREIGN PATENTS OR APPLICATIONS
1,047,082  10/1966  United Kingdom

OTHER PUBLICATIONS
Chem. Abstracts, vol. 70, 87171.

*Primary Examiner*—James O. Thomas, Jr.
*Assistant Examiner*—James H. Reamer
*Attorney, Agent, or Firm*—Armstrong, Nikaido & Wegner

[57] ABSTRACT

Trifluoromethylthiophenylethylamine derivatives, made from the corresponding acid chlorides by successive reduction, condensation with nitroethane, reduction, and condensation with an amide, possess anorexigenic properties, unaccompanied by central stimulant activity or cardiovascular effects.

2 Claims, No Drawings

PHENYL PROPANONES

The present invention provides the phenylethylamine derivatives of the formula:

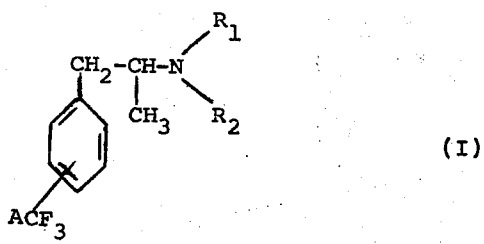

(I)

in which $R_1$ and $R_2$ are identical or different and represent hydrogen atoms or straight or branched alkyl radicals of 1 to 5 carbon atoms, or $R_1$ and $R_2$, together with the nitrogen atom, form a heterocyclic radical which may contain one or more other hetero-atoms, for example a piperidino, morpholino or thiomorpholino radical, and A represents sulphur or oxygen, and their acid addition salts with pharmaceutically acceptable organic and inorganic acids.

In view of the existence of an asymmetric carbon atom in the molecule of the compounds of formula (I), they exist in racemic and optically active forms, and it is to be understood that all such forms are within the scope of the invention.

Pharmacological investigation of the compounds of formula (I), as the hydrochlorides, has shown that they possess powerful anorexigenic properties. However, unlike the majority of amphetamine derivatives, they are devoid of (1) central stimulant activity, especially at the level of the cortex; and (2) cardiovascular effects such as tachycardia and increase in the arterial pressure. These properties make the compounds of formula (I) and their salts very valuable in therapy, especially for the treatment of various forms of obesity.

The invention thus includes within its scope pharmaceutical compositions comprising a compound of formula (I), as base or pharmaceutically acceptable salt thereof, and a compatible pharmaceutical carrier, especially one such as to provide a composition suitable for oral administration, e.g. as a pill, tablet, powder, syrup or elixir.

According to a feature of the invention, the compounds of formula (I) are prepared by condensing a 1-phenyl-2-propanone of the formula:

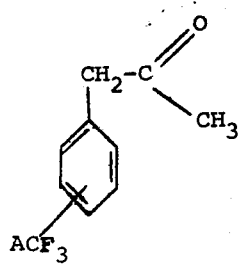

(II)

in which A is as hereinbefore defined, with an amine of formula:

(III)

in which $R_1$ and $R_2$ are as hereinbefore defined, and, if desired, converting a base obtained into an acid addition salt thereof.

This condensation is preferably carried out at elevated temperature in the presence of formic acid, using a large excess of the amine, preferably at 160° to 170°C, for 10 to 20 hours, preferably about 14 hours. The compound of formula (I) may be isolated either as a base or as a salt, preferably the hydrochloride.

The compounds of formula (II) are new. They are prepared by reducing a 1-phenyl-2-nitro-propene of the formula:

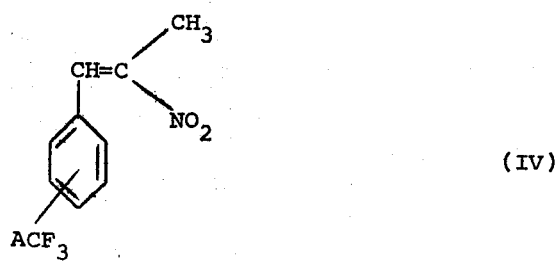

(IV)

in which A is oxygen or sulphur, for example with a mixture of iron and hydrochloric acid, in the presence of ferric chloride. This reduction is preferably carried out at 90°C., by heating for a few hours at this temperature. The 1-phenyl-2-nitro-1-propene may be isolated by steam distillation after the reaction mixture has been rendered alkaline.

The 1-phenyl-2-nitro-propenes of formula (IV) are also new. They are made by condensing a benzaldehyde of the formula:

(V)

in which A is oxygen or sulphur, with nitro-ethane in the presence of a catalytic amount of an aliphatic amine, for example n-butylamine. This reaction may be carried out by heating the mixture at the reflux temperature of nitro-ethane and separating the water produced as it is formed.

The aldehydes of formula (V) are also new. They are made by reducing a benzoic acid chloride of the formula:

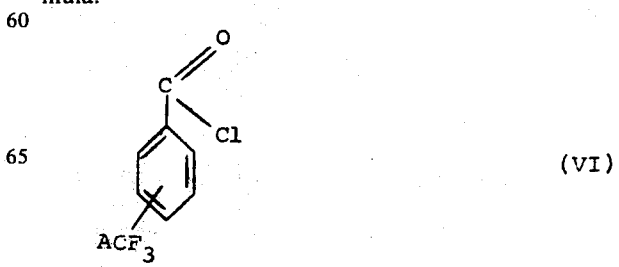

(VI)

in which A is oxygen or sulphur, with hydrogen in the presence of palladium, for example, in toluene, in the presence of a catalytic amount of 5% strength palladium on barium sulphate. The temperature of the reaction is the reflux temperature of the solvent employed, and its duration is from 10 to 15 hours, preferably about 12 hours. The aldehyde of formula (V) is isolated by combining it with sodium bisulphite, and then decomposing the compound obtained by heating in water in the presence of potassium carbonate and steam distillation of the aldehyde (V).

The amines of formula (I) may be resolved into their optical antipodes by any known means, for example by fractional crystallisation of their salts with an optically active acid, preferably d-tartaric acid or d-dibenzoyltartaric acid.

The following Examples illustrate the invention.

EXAMPLE 1

1-(3'-Trifluoromethylthio-phenyl)-2-ethylamino-propane 1.85 g (40 mmols) of formic acid are introduced into a 50 ml. two-necked flask equipped with an air condenser and a dropping funnel. The flask is cooled on an ice bath and 2 ml. of ethylamine are added dropwise. The reaction mixture is allowed to return to ambient temperature and 2.85 g. (10 mmols) of 1-(3'-trifluoromethylthio-phenyl)-2-propanone are added. The contents of the flask are heated for 14 hours at 160°–170°C., 2 ml. of concentrated hydrochloric acid and 2 ml. of water are added, and the mixture is heated for 3 hours at the reflux temperature. A further 2 ml. of concentrated hydrochloric acid are added and the mixture is heated again at the reflux temperature for 2 hours. The mixture is allowed to cool, water is added and the product is extracted once with 50 ml. of diethyl ether. The aqueous layer is rendered alkaline with sodium hydroxide solution and extracted three times in succession with 50 ml. of diethyl ether each time. The combined ether extracts are washed several times with water, dried over sodium sulphate, and filtered. The ether is evaporated from the filtrate in vacuo on a water bath. The 1.4 g of oily residue are dissolved in anhydrous diethyl ether and a solution of hydrogen chloride in diethyl ether is added until precipitation has ended.

1-(3'-Trifluoromethylthio-phenyl)-2-ethylaminopropane hydrochloride, recrystallised from ethyl acetate, is obtained as a white crystalline compound which is soluble in water, m.p. 130°C. Yield: 30 per cent.

Analysis $C_{12}H_{17}ClF_3NS$ (M.W. = 299.8)

| | C 48.07 | H 5.71 | N 4.67 | Cl 11.83; |
|---|---|---|---|---|
| Calculated %: | 48.19 | 5.67 | 4.66 | 11.97 |
| Found %: | 48.15 | 5.62 | — | 11.87. |

EXAMPLE 2

1-(3'-Trifluoromethylthio-phenyl)-2-propanone.

13.2 g. (50 mmols) of 1-(3'-trifluoromethylthio-phenyl)-2-nitro-propene, 19.6 g. (0.35 g. atom) of iron powder and 0.25 g. of ferric chloride are introduced into a 250 ml. three-necked flask equipped with a mechanical stirrer, a condenser and a dropping funnel, and this mixture is heated on an oil bath at 80°–90°C. 13.5 ml. of concentrated hydrochloric acid are added dropwise, via the dropping funnel, with stirring, over the course of 7 hours, while the temperature is kept at 90°C. The reaction mixture is allowed to cool and rendered alkaline with sodium hydroxide solution. The ketone is then steam distilled. The distillate is extracted twice in succession with 100 ml. of diethyl ether each time. The two ether extracts are combined, dried over sodium sulphate and filtered. The solvent is evaporated from the filtrate in vacuo on a water bath, and the residue is rectified. 7.1 g. (60.5% yield) of 1-(3'-trifluoromethylthiophenyl)-2-propanone are thus obtained as a colourless oil, b.p. 138°–146°C./25-30 mm. Hg., $n_D^{23°}$ = 1.489.

Analysis $C_{10}H_9F_3OS$ (M.W. = 234)

| Calculated %: | C 51.28 | H 3.88; |
|---|---|---|
| Found %: | 50.99 | 3.90 |
| | 51.29 | 3.66. |

EXAMPLE 3

1-(3'-Trifluoromethylthio-phenyl)-2-nitro-1-propene.

33.3 g. (16 mmols) of 3-trifluoromethylthiobenzaldehyde, 43.3 ml. of nitro-ethane and 2 ml. of n-butylamine are introduced into a 250 ml. flask equipped with a Dean and Stark trap surmounted by a condenser. The mixture is heated for 4 hours at the reflux temperature and then rectified. After the nitro-ethane has been removed, 26.8 g. (64% yield) of 1-(3'-trifluoromethylthio-phenyl)-2-nitro-1-propene, b.p. 130°–138°C./8–9 mm.Hg., are collected. This compound is dissolved in petroleum ether (b.p. 35°–70°C.) and the solution is chilled overnight. 1-(3'-Trifluoromethylthio-phenyl)-2-nitro-1-propene is finally obtained as a crystalline solid, m.p. 48°C.

Analysis $C_{10}H_8F_3NO_2S$ (M.W. = 263)

| Calculated %: | C 45.63 | H 3.06; |
|---|---|---|
| Found % | 45.35 | 3.13 |
| | 45.50 | 2.85. |

EXAMPLE 4

3-Trifluoromethylthio-benzaldehyde.

A solution of 56.9 g. (237 mmols) of 3-trifluoromethyl-thiobenzoic acid chloride in 285 ml. of anhydrous toluene and 5.7 g. of 5 per cent strength palladium on barium sulphate is introduced into a one litre three-necked flask equipped with a condenser, a mechanical stirrer and a gas bubbler tube. This mixture is heated, with stirring, for 12 hours at the reflux temperature, while a gentle stream of hydrogen is bubbled through it. The catalyst is filtered off and washed with diethyl ether. 125 ml. of a solution of sodium bisulphite (d = 1.33) are added to the filtrate. This mixture is stirred vigorously for 24 hours and the bisulphite compound is filtered off, washed with diethyl ether and introduced into a three-necked flask. A solution of 80 g. of potassium carbonate in 500 ml. of water is added and the mixture is boiled, so as to steam distil the aldehyde as it is formed. The distillate is extracted twice in succession with diethyl ether. The combined ether phases are dried over sodium sulphate and filtered. The solvent is evaporated in vacuo on a water bath and the residue is rectified. 33.3 g. (67% yield) of 3-trifluoromethylthio-benzaldehyde, as an oil, b.p. 108°–111°C./30-38 mm.Hg., are thus obtained.

Analysis $C_8H_5F_3OS$ (M.W. = 206)

| Calculated %: | C 46.60 | H 2.45: |
| --- | --- | --- |
| Found %: | 46.54 | 2.41 |
|  | 46.35 | 2.46. |

EXAMPLE 5

1-(3'-Trifluoromethoxy-phenyl)-2-ethylamino-propane and its hydrochloride 13 ml (0.2 mol) of ethylamine are introduced into a 250 ml. two-necked flask equipped with an air condenser and a dropping funnel and cooled on an alcohol-carbon dioxide ice bath. 9.65 ml (0.25 mol) of formic acid are added dropwise. The reaction mixture is allowed to return to ambient temperature and 14.15g (65 mmols) of 1-3(3'-trifluoromethoxy-phenyl)-2-propanone are added. The contents of the flask are heated for 20 hours at 150°C. After cooling 20 ml of concentrated hydrochloric acid and 20 ml of water are added, and the mixture is heated for 5 hours at the reflux temperature. A large amount of water is added and the product is extracted with 100 ml of diethyl ether. The aqueous layer is rendered alkaline with sodium hydroxide solution and extracted three times in succession with 100 ml of diethyl ether each time. The combined ether extracts are washed several times with water, dried over sodium sulphate, and filtered. The ether is evaporated from the filtrate in vacuo on a water bath.

The residue is rectified 8,7 g (70 % yield) of 1-(3'-trifluoromethoxy-phenyl)-2-ethylamino-propane are thus obtained as a liquid, b.p. 108°–110°/16mm Hg.

Analysis $C_{12}H_{16}F_3NO$ (M.W. = 247,27)

| Calculated % | C 58.31 | H 6.56 | N 5.66 |
| --- | --- | --- | --- |
| Found % | 58.58 | 6.67 | 5.59 |

To prepare the hydrochloride, the above base is dissolved in anhydrous diethyl ether and a solution of hydrogen chloride in diethyl ether is added until precipitation has ended, so as to obtain 1-(3'-trifluoromethoxy-phenyl)-2-ethylaminopropane hydrochloride, m.p. 132° C.

Analysis $C_{12}H_{17}ClF_3NO$ (M.W. = 283.8)

| Calculated %: | C 5.80 | H 6.04 | Cl 12.49 |
| --- | --- | --- | --- |
| Found %: | 5.83 | 5.77 | 12.52 |

EXAMPLE 6

1-(3'-Trifluoromethoxy-phenyl)-2-propanone.

29g (117 mmols) of 1-(3'-trifluoromethoxy-phenyl)-2-nitro-propene, 46g (0.82g atom) of iron powder, 0.6g. of ferric chloride and 120 ml of water are introduced into a 500 ml. threenecked flask equipped with a mechanical stirrer, a condenser and a dropping funnel, and this mixture is heated at 80°C. 29 ml. of concentrated hydrochloric acid are added dropwise, via the dropping funnel, with stirring, over the course of 5 hours, while the temperature is kept at 80°C. The reaction mixture is allowed to cool overnight. The ketone is then steam distilled. The distillate is extracted twice in succession with 100 ml. of diethyl ether each time. The two ether extracts are combined, dried over sodium sulphate and filtered. The solvent is evaporated from the filtrate in vacuo on a water bath, and the residue is rectified. 14,15g (55 % yield) of 1-(3'-trifluoromethoxy-phenyl)-2-propanone are thus obtained as a liquid, b.p. 112°–118°C./18mm.Hg., $n_D^{21°} = 1.448$

EXAMPLE 7

1-(3'-Trifluoromethoxy-phenyl)-2-nitro-1-propene.

32g. (0.17 mols) of 3-trifluoromethoxy-benzaldehyde, 32ml. of nitro-ethane and 2ml. of n-butylamine are introduced into a 100 ml. flask surmounted by a condenser. The mixture is heated for 20 hours at the reflux temperature and then rectified. 29g (70 % yield) of 1-(3'-trifluoromethoxy-phenyl)-2-nitro-1-propene are collected as a yellow oil b.p. 90°–110° C./2 mm.Hg.,

EXAMPLE 8

3-Trifluoromethoxy-benzaldehyde 103 g. (0.544 mol) of stannous chloride and 400 ml of diethyl ether are introduced into a one litre three-necked flask equipped with a condenser, a mechanical stirrer and a gas bubbler tube. This mixture is cooled and saturated with hydrogen chloride gas until the stannous chloride is completely dissolved. A solution of 72.7g. (0.388 mol) of 3-trifluoromethoxy-benzonitrile in 75 ml. of anhydrous diethyl ether is added dropwise but fastly via the dropping funnel, while the mixture is cooled with ice-water. The mixture is allowed overnight, then the aldehyde is steam distilled. The distillate is extracted several times with diethyl ether and the extracts are combined. 250 ml. of a solution of sodium bisulphite ($d=1.32$-$1.33$) are added to the extracts and allowed overnight. The bisulfite compound is filtered off, washed with a small quantity of ice-water and then with diethyl ether. The compound is introduced into a one litre flask which contains solution of 60 g. of potassium carbonate in 250 ml. of water. The mixture is heated at 100°C so as to decompose the bisulfite compound and to steam distil the aldehyde as it is formed. The distillate is extracted several times with diethyl ether. The combined ether phases are dried over sodium sulphate and filtered and the solvent is evaporated. 32g. (44% yield) of 3-trifluoromethoxy-benzaldehyde are obtained as a colourless oil.

EXAMPLE 9

1-(3'-Trifluoromethylthio-phenyl)-2-amino-propane and its hydrochloride 3.5g. (0.2 mol) of liquid ammoniac are introduced into a 250 ml. two-necked flask equipped with an air condenser and a dropping funnel and cooled on an alcohol-carbon dioxide ice bath. 9,7 ml. of formic acid are added dropwise via the dropping funnel. The reaction mixture is allowed to return to ambient temperature and 15,1g. (65 mmols) of 1-(3'-trifluoromethylthio-phenyl)-2-propanone are added. The contents of the flask are heated for 23 hours at 155°–160°C. After cooling 30 ml. of concentrated hydrochloric acid are added, and the mixture is heated for 7 hours at the reflux temperature. A large amount of water is added and the product is extracted with 100 ml. of diethyl ether. The aqueous layer is rendered alkaline with sodium hydroxide solution and extracted three times in succession with 100ml. of diethyl ether each time. The combined ether extracts are washed several times with water, dried over sodium sulphate, and filtered. The ether is evaporated from the filtrate in vacuo on a water bath. 8g. (52 % yield) of 1-(3'-trifluoromethylthiophenyl)-2 amino-propane are thus obtained as a slightly yellow oil.

Analysis $C_{10}H_{12}F_3NS$ (M.W. = 235.27)

| | | | | | |
|---|---|---|---|---|---|
| Calculated % | C 51.05 | H 5.14 | F 24.23 | N 5.95 | S 13.63 |
| Found % | 51.12 | 5.03 | 24.75 | 6.04 | 13.29 |

The above base is dissolved in anhydrous diethyl ether and a solution of hydrogen chloride in diethyl ether is added until precipitation has ended so as to obtain 1-(3'-trifluoromethylthio-phenyl)-2-amino-propane hydrochloride.

Analysis $C_{10}H_{13}Cl\ F_3NS$ (M.W. = 271.73)

| | | | | | | |
|---|---|---|---|---|---|---|
| Calculated % | C 44.20 | H 4.82 | Cl 13.05 | F 20.98 | N 5.18 | S 11.80 |
| Found % | 44.17 | 4.90 | 12.92 | 21.30 | 5.00 | 12.02 |

Pharmacological investigation of the compounds has shown that they are very valuable in therapy.

In view of the lightening of the report, the investigated compounds are referred as follows:

A: compound of example 1 (hydrochloride)
   in racemic form: $A_r$
   in dextrorotatory form: $A_d$
   in levorotatory form: $A_l$
B: compound of example 5 (hydrochloride)
   in racemic form: $B_r$
   in dextrorotatory form: $B_d$
   in levorotatory form: $B_l$
C: compound of example 9 (hydrochloride)
   in racemic form: $C_r$ The investigation has shown that all of them but the two levorotatory isomers possess powerful anorexigenic properties.

These properties have been displayed by measuring in strict standard conditions the food quantities absorbed by rats which were previously accustomed to receive their food every day within a 6 hours period. The experiments have been carried out by administering each compound in several doses and determinating graphically the 50 % active dose DA 50 (doses able to reduce the consumption of food of 50 %) The compounds of this invention are compared to fenfluramine (in racemic form)

The following DA 50 were found:

| compound | DA 50 (mg/kg) |
|---|---|
| Fenfluramine | 10 |
| $A_r$ | 4.5 |
| $A_d$ | 2.5 |
| $A_l$ | >10 |
| $B_r$ | 9 |
| $B_d$ | 4.5 |
| $B_l$ | >10 |
| $C_r$ | 5 |

The anorexigenic activity of the dextrorotatory compounds is very high, up to 4 times that of fenfluramine. The racemic compounds are also more active than fenfluramine and the results show that in fact their activity is due to the dextrorotatory isomer for the levo compounds are much less active.

The acute toxicity of the compounds is moderate and equal or slightly inferior to that of fenfluramine (even in the case of the most active compound) and is the same for the dextro or the levorotatory isomer.

As a result of these considerations, the compounds of the invention in racemic or dextrarotatory form possess a much better therapeutic index (up to 4 times) than fenfluramine.

These compounds are remarkable for the lack of the most characteristic secondary effects of amphetamine derivatives: on the one hand, they are devoid of central stimulent activity, which is shown by actimetry and group toxicity experiments; on the other hand, they are distinctive from any amphetamine derivative, including fenfluramine, by the lack of general hypertensive activity and especially by the lack of effects in the pulmonary arterial pressure.

| anesthetized dog | increase in the arterial pressure | |
|---|---|---|
| | carotid | pulmonary |
| Fenfluramine | significant from 0.5 mg/kg | significant from 1 mg/kg |
| $A_r$ | none up to 5 mg/kg | non up to 5 mg/kg |
| $A_d$ | none or non significant up to 2 mg/kg | none or non significant up to 2 mg/kg |

The compounds of this invention are thus remarkable both for their anorexigenic activity -which is higher than that of fenfluramine- and for they are devoid of secondary effects. These properties make the compounds of formula (I) and their salts very valuable in therapy, especially for the treatment of various forms of obesity.

They may be administered in the amount of 10 to 50 mg daily.

We claim:

1. A 1-phenyl-2-propanone of the formula:

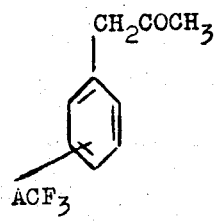

in which A is sulphur.

2. 1-(3'-Trifluoromethoxyphenyl)-2-propanone.

* * * * *